United States Patent [19]
Kidani

[11] Patent Number: 6,008,395
[45] Date of Patent: Dec. 28, 1999

[54] PLATINUM (IV) COMPLEX, PRODUCTION PROCESS THEREOF AND CARCINOSTATIC AGENT CONTAINING THE SAME

[76] Inventor: Yoshinori Kidani, 13-11, Kataseyama 3-chome, Fujisawa-shi, Kanagawa-ken 251, Japan

[21] Appl. No.: 08/894,563
[22] PCT Filed: Feb. 28, 1996
[86] PCT No.: PCT/JP96/00463
   § 371 Date: Nov. 3, 1997
   § 102(e) Date: Nov. 3, 1997
[87] PCT Pub. No.: WO96/26949
   PCT Pub. Date: Sep. 6, 1996

[30] Foreign Application Priority Data

Feb. 28, 1995 [JP] Japan .................................. 7-039983

[51] Int. Cl.$^6$ .................................................. C07F 15/00
[52] U.S. Cl. ........................................................ 556/137
[58] Field of Search ............................................. 556/137

[56] References Cited

U.S. PATENT DOCUMENTS

| 4,845,124 | 7/1989 | Kidani et al. . | |
| 5,194,645 | 3/1993 | Barnard .................................. | 556/137 |
| 5,244,919 | 9/1993 | Abrams et al. ......................... | 514/492 |
| 5,393,909 | 2/1995 | Khokhar .................................. | 556/137 |

FOREIGN PATENT DOCUMENTS 1-294684  11/1989  Japan .
4-327596  11/1992  Japan .

OTHER PUBLICATIONS

Platinum and Other Metal Coordination Compounds in Cancer Chemotherapy, Edited by Stephen B. Howell pp. 93–100 (1991).

Platinum and Other Metal Coordination Compounds in Cancer Chemotherapy, Edited by Stephen B. Howell pp. 391–399 (1991).

Journal of the Chemical Society of Japan, Chemistry and Industrial Chemistry, No. 4, pp. 675–683 (1988.

Cancer Research 52, pp. 822–828, Feb. 15, 1992.

Br. J. Cancer (1994), 70, 415–420.

Journal of Inorganic Biochemistry, 54, 39–47 (1994).

Barnard, Inor Chem "Studies on the Oral Anticancer Drug JM216: Synthesis and Characterization of Isomers and Related Complexes", 35, pp. 3280–3284, Feb. 1996.

*Primary Examiner*—Gary Geist
*Assistant Examiner*—Jean F Vollano
*Attorney, Agent, or Firm*—Oblon, Spivak, McClelland, Maier & Neustadt, P.C.

[57] ABSTRACT

A platinum(IV) complex represented by the general formula (I):

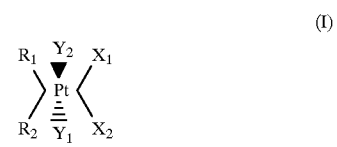

wherein $R_1$ and $R_2$ independently represent ammonia, an alkylamine or a cycloalkylamine, or $R_1$ and $R_2$ may together form a cycloalkyldiamine; $X_1$ and $X_2$ independently represent a halogen, nitrate ion, sulfate ion or a monocarboxylic acid, or $X_1$ and $X_2$ may together form a glycolate or a dicarboxylic acid; $Y_1$ represents formic acid, a $C_1$–$C_8$ alkyl-, alkenyl-, aryl-, aralkyl-, alkylamino- or alkoxyl-monocarboxylic acid or sulfonic acid; and $Y_2$ represents a halogen. The complex of the invention is stable even when orally administered and has high antitumor activity.

8 Claims, 2 Drawing Sheets

PLATINUM (IV) COMPLEX, PRODUCTION PROCESS THEREOF AND CARCINOSTATIC AGENT CONTAINING THE SAME

This application is the national phase of PCT/JP96/00463 filed Feb. 26, 1996.

TECHNICAL FIELD

This invention relates to a novel platinum(IV) complex which shows strong antitumor activity, a process for the production thereof and a carcinostatic agent that contains the same.

BACKGROUND ART

Since the development and practical use of cisplatin as an effective antitumor agent, a broad range of studies have been conducted with the aim of finding a new platinum complex which possesses more effective antitumor activity than cisplatin, and of improving properties thereof other than the antitumor action, such as reduction of toxicity and other undesirable side effects.

Carboplatin is known as a platinum(II) complex, as well as recently developed oxaliplatin. With regard to platinum (IV) complexes, iproplatin is known, and tetraplatin has been subjected to clinical trial but its clinical development has been suspended due to the side effects, such as toxicity.

Each of these platinum complexes is for parenteral administration use and is hydrophilic. In order to improve quality of life of cancer patients, great concern has been directed toward the development of an oral preparation for use in the treatment of cancer patients at the terminal stage.

DISCLOSURE OF THE INVENTION

The present invention provides platinum(IV) complexes having high antitumor activity, particularly for use in oral administration. Many of these complexes show high solubility in both water and organic solvents, have high partition coefficient and are stable in strongly acidic solution.

The present invention is a platinum(IV) complex represented by the general formula (I):

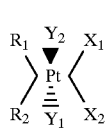

(I)

wherein $R_1$ and $R_2$ independently represent ammonia, an alkylamine or a cycloalkylamine, or $R_1$ and $R_2$ may together form a cycloalkyldiamine; $X_1$ and $X_2$ independently represent a halogen, nitrate ion, sulfate ion or a monocarboxylic acid, or $X_1$ and $X_2$ may together form a glycolate or a dicarboxylic acid; $Y_1$ represents formic acid, a $C_1$–$C_8$ alkyl-, alkenyl-, aryl-, aralkyl-, alkylamino- or alkoxyl-monocarboxylic acid or sulfonic acid; and $Y_2$ represents a halogen.

In the general formula (I), the alkylamine includes normal and iso forms, and examples of the cycloalkyldiamine include cyclopentyldiamine, cyclohexyldiamine, cycloheptyldiamine and cyclooctyldiamine, each of which may be a cis, trans-d or trans-l isomer of 1,2-, 1,3- or 1,4-form, 1,1-diaminomethylcyclohexane, 1,1-diaminocyclopentane, 1,1-diaminocycloheptane, 1,1-diaminocyclooctane, cis-d, cis-l, trans-d and trans-l isomers of 1-aminomethyl-2-aminomethylcyclohexane and cis-dl and trans-dr isomers thereof, cis-d, cis-l, trans-d and trans-l isomers of 1-aminomethyl-2-aminomethylcyclopentane and cis-dl and trans-dl isomers thereof, cis-d, cis-l, trans-d and trans-l isomers of 1-aminomethyl-2-aminomethylcycloheptane and cis-dl and trans-dl isomers thereof, cis-d, cis-l , trans-d and trans-e isomers of 1-aminomethyl-2-aminomethylcyclooctane and cis-dl and trans-dl isomers thereof and the like.

In the general formula (I), examples of the monocarboxylic acid include gluconic acid, glucuronic acid and the like sugar carboxylic acids and an alkyl monocarboxylic acid, and examples of the dicarboxylic acid include oxalic acid, malonic acid and derivatives thereof (such as of methyl, ethyl, benzyl, benzoyl or the like) and 1,1-cyclobutanedicarboxylic acid.

BEST MODE OF CARRYING OUT THE INVENTION

Figure 1:
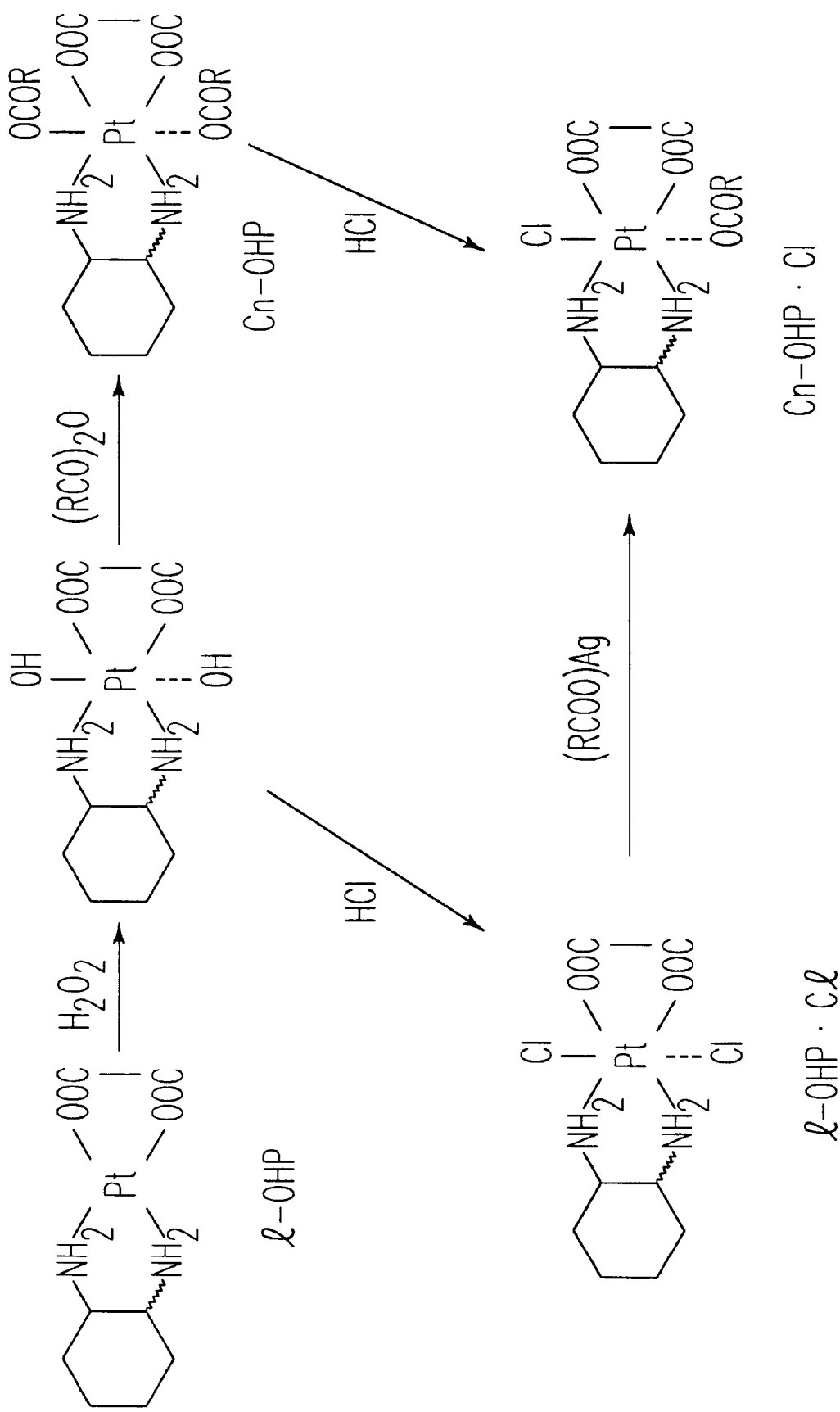
FIG. 1 shows a reaction scheme regarding the process for the production of the platinum(IV) complex of the present invention.

A preferred platinum complex of the present invention is a complex represented by the general formula (II):

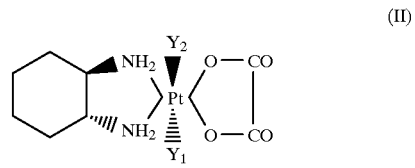

(II)

wherein $Y_1$ and $Y_2$ are as defined in the general formula (I).

A more preferred platinum complex of the present invention is a platinum complex represented by the general formula (II) wherein $Y_1$ is a $C_2$–$C_8$ alkyl monocarboxylic acid and $Y_2$ is a halogen.

A characteristic nature of the present invention is that a monocarboxylic acid or a sulfonic acid and a halogen element are coordinated simultaneously at the trans position.

The following shows abbreviations to be used herein. cis, trans, cis: c-t-c dach: 1,2-cyclohexanediamine (cis-dach, R,S-dach; trans-d-dach,
1S,2S-dach; trans-2-dach, 1R,2R-dach)
amcha: 2(aminomethyl)cyclohexylamine (cis-d, 1S,2S-amcha; cis-l,
1R,2R-amcha; trans-d, 1S,2R-amcha; trans-l, 1R,2S-amcha)
C5-OHP: t,c,c- [Pt (OCOC$_4$H$_9$)$_2$(ox) (1R,2R-dach)]
lQ-OHP: [Pt(ox) (1R,2R-dach)]
C5-OHP-Cl: t,t,c,c-[PtCl(OCOC$_4$H$_9$)(ox)(1R,2R-dach)]
C5-OHP-Br: t,t,c,c-[PtBr(OCOC$_4$H$_9$)(ox)(1R,2R-dach)]
C5-OHP-I: t,t,c,c-[PtI(OCOC$_4$H$_9$)(ox)(1R,2R-dach)]
C4-OHP: t,c,c- [Pt (OCOC$_3$H$_7$)$_2$(ox) (1R,2R-dach)]
C4-OHP-Hal: t,t,c,c-[PtHal(OCOC$_3$H$_7$)(ox)(1R,2R-dach)]
C6-OHP: t,c,c- [Pt (OCOC$_5$H$_{11}$)$_2$ (ox) (1R,2R-dach)]
C6-OHP-Hal: t, t,c,c-[PtHal(OCOC$_5$H$_{11}$) (ox) (1R,2R-dach)]
l-OHP Cl: t-[PtCl$_2$(ox)(1R,2R-dach)]
l-OHP-Br: t-[PtBr$_2$(Ox)(1R,2R-dach)]

l-OHP-I: t-[PtI$_2$(ox)(1R,2R-dach)]
C4-COOAg: Ag-butylate
C5-COOAg: Ag-valerate
C6-COOAg: Ag-hexanoate
C7-COOAg: Ag-heptanoate
Hal: Cl, Br, I or F
ox: oxalate
mal: malonate
cbdca: 1,1-cyclobutane dicarboxylate
HPLC: high performance liquid chromatography It was found that, when C4-OHP, C5-OHP, C6-ORP or the like Cn-OHP is orally administered, one carboxylic acid thereof is gradually substituted by Cl in the strongly acidic gastric juice (1 N HCl, pH 0.1).

When C5-OHP is allowed to undergo 24 hours of reaction in a strong acid and then subjected to separation by HPLC, [PtCl(OCOC$_4$H$_9$) (oxalato) (1R,2R-dach)], namely C5.OHP Cl, can be produced. In the same manner, [PtCl(OCOC$_3$H$_7$) (oxalato) (1R,2R-dach)], namely C4-OHP.Cl, [PtCl (OCOC$_5$H$_{11}$) (oxalato) (1R,2R-dach)], namely C6-OHP.Cl, and [PtCl(OCOC$_6$H$_{13}$) (oxalato) (1R,2R-dach)], namely C7-OHP.Cl, can be produced from C4-OHP, C6-OHP and C7-OHP, respectively.

The platinum complex of the present invention can also be synthesized by the following alternative method. A methanol solution of l-OHP-Cl(or Br or I) as [PtCl$_2$(or Br$_2$ or I$_2$)(oxalato)(1R,2R-dach)] is allowed to undergo 24 hours of reaction, while stirring in the dark at room temperature, with 1M of C5-COOAg (this can be obtained as white precipitate by adding silver nitrate to n-valeric acid and then adding alcohol thereto; C4-COOAg, C6-COOAg, C7-COOAg and the like can also be synthesized in the same manner and used instead thereof). After filtering off the thus formed AgCl, methanol is evaporated, the residue is dissolved in ethanol, activated carbon is added to the solution and filtered off and then water is added to the filtrate to collect the thus formed precipitate by filtration. In the same manner, C4-OHP.Cl, C6-OHP.Cl and C7-OHP.Cl can be produced.

By using l-OHP.Cl, l-OHP.Br or l-OHP.I as the starting material and allowing it to react with C4-COOAg, C5-COOAg, C6-COOAg or C7-COOAg, a large amount of C4-OHP.Cl(or Br or I), C5-OHP.Cl(or Br or I), C6-OHP.Cl (or Br or I) or C7-OHP.Cl(or Br or I) can be produced. According to this process, various types of complexes can be produced from C$_{1-8}$COOAg.

The aforementioned two synthetic processes are shown in FIG. 1.

The platinum(IV) complexes of the present invention show antitumor activity when orally administered for the treatment of malignant tumors. In consequence, these complexes can be made into dosage forms suitable for oral administration, such as tablets, pills, capsules, liposome inclusions and sterile suspensions, as well as suppositories, liniments, ointments, solutions and the like. Usual pharmaceutical carriers, additives, binders and/or fillers can also be used. They can be used also for parenteral administration as freeze-dried preparations and solutions.

As fillers, diluents and auxiliaries of oral administration preparations, one or more materials can be used which may be selected from lactose, sucrose, glucose, sorbitol, mannitol, potato starch, amylopectin, other various starches, cellulose derivatives (for example, carboxymethyl cellulose, hydroxyethyl cellulose and the like), gelatin, magnesium stearate, polyvinyl alcohol, calcium stearate, polyethylene glycol, gum arabic, talc, titanium dioxide, vegetable oils such as olive oil, peanut oil, sesame oil and the like, paraffin oils, neutral fat bases, ethanol, propylene glycol, physiological saline, sterile water, glycerol and the like.

As fillers for injection use, sugar solutions, buffer solutions, ethylene glycol, polyethylene glycol and the like can be used.

It is desirable to use the complex of the present invention in an amount of from 0.01 to 200 mg/kg, preferably from 0.1 to 100 mg/kg, more preferably from 0.5 to 50 mg/kg, in the case of parenteral administration, or from 0.1 to 2,000 mg/kg, preferably from 1 to 1,000 mg/kg, more preferably from 5 to 500 mg/kg, in the case of oral administration.

The platinum complex of the present invention does not show renal toxicity, cross-resistance, mutagenicity and the like which become medicinal problems.

EXAMPLES

Examples of the present invention are given below by way of illustration and not by way of limitation.

Example 1

Formation of C4-OHP.Cl

A 0.2 g portion of C4-OHP was dissolved in 20 ml of 1 N HCl and allowed to stand for 12 hours at 37° C. in the dark. After the reaction, the product was separated and purified by HPLC. Yield, 18 mg as colorless powder.

HPLC: Using Cosmosil 5C18 columns of 10 mm i.d. x 5 cm (guard column) and 15 mm i.d. x 25 cm (main column), 0.8 ml of the sample solution was injected and eluted at 50° C. with 30% MeOH at a rate of 3 ml/min.

Example 2

Formation of C5-OHP.Cl

A 0.4 g portion of C5-OHP was dissolved in 20 ml of 30% MeOH-1 N HCl mixture solution and allowed to stand for 30 hours at 37° C. in the dark. After the reaction, the product was separated and purified by HPLC. Yield, 35 mg as colorless powder.

HPLC was carried out under the same conditions as described in Example 1.

Example 3

Formation of C6-OHP.Cl

A 0.4 g portion of C6-OHP was dissolved in 17 ml of 50% MeOH-1 N HCl mixture solution and allowed to stand for 36 hours at 37° C. in the dark. After the reaction, the product was separated and purified by HPLC. Yield, 35 mg as colorless powder.

HPLC was carried out under the same conditions as described in Example 1.

Figure 2:
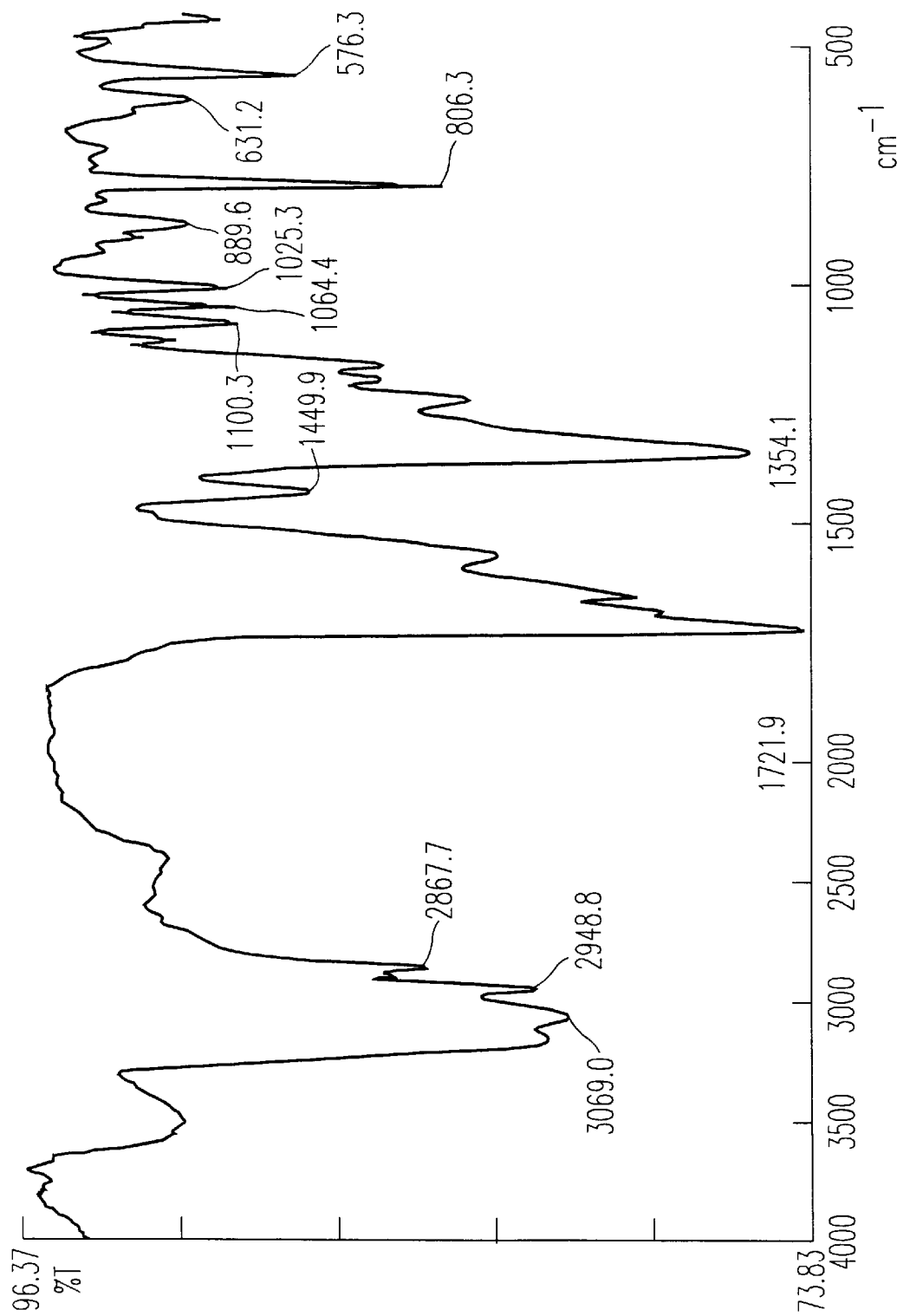
FIG. 2 is a chart showing infrared absorption spectrum of C6-OHP.Cl as a member of the platinum(IV) complex of the present invention.

Infrared absorption spectrum of the thus obtained C$_6$-OHP.Cl is shown in FIG. 2, and results of the TLC analysis (development solvent: butanol/acetic acid/water= 12:3:5) are shown below.

| Complex | R$_f$ value |
| --- | --- |
| l-OHP | 0.13 |
| l-OHP · Cl (starting material) | 0.24 |
| C6-OHP · Cl | 0.29 |
| C6-OHP | 0.31 |

Example 4

Synthesis of C5-OHP.Br

A 1.12 g portion of [PtBr2(ox)(1R,2R-dach)], namely l-OHP.Br, was dissolved in 140 ml of hot MeOH, and the solution was mixed with 0.42 g of 1M C5-COOAg and stirred for 48 hours at room temperature in the dark. After the reaction, the thus formed precipitate of AgBr was filtered off, MeOH was evaporated to dryness, the resulting residue was dissolved in 30 ml of EtOH, activated carbon was added to the solution and filtered off and then the filtrate was concentrated and subjected to alumina or silica gel column chromatography to effect separation (from the starting material and C5-OHP) and purification. Yield, 0.85 g, 73%, as light yellow powder.

Example 5

Synthesis of C6-OHP.Br

A 1.12 g portion of l-OHP.Br was dissolved in 140 ml of MeOH, and the solution was mixed with 0.44 g of 1M C6-COOAg and stirred for 48 hours at room temperature in the dark. After the reaction, the thus formed AgBr was filtered off to carry out purification by the same treatment as described in Example 4. Yield, 0.95 g, 80%, as light yellow powder.

Example 6

Synthesis of C5-OHP.I

A 0.65 g portion of l-OHP.I was dissolved in 100 ml of MeOH, and the solution was mixed with 0.21 g of 1M C5-COOAg and stirred for 48 hours at room temperature in the dark. Thereafter, the same treatment as in Example 4 was repeated. Yield, 0.45 g, 72%.

Example 7

Synthesis of C6-OHP.I

A 0.65 g portion of l-OHP.I was dissolved in 100 ml of MeOH, and the solution was mixed with 0.22 g of 1M C6-COOAg and stirred for 48 hours at room temperature in the dark. Thereafter, the same treatment as in Example 4 was repeated. Yield, 0.45 g, 71%.

Example 8

Synthesis of C5-OHP.Cl

A 0.47 g portion of l-OHP.Cl was dissolved in 40 ml of $H_2O$+MeOH mixture solution, and the solution was mixed with 0.21 g of 1M C5-COOAg and stirred for 48 hours at room temperature in the dark. Thereafter, the same treatment as in Example 4 was repeated. Yield, 0.45 g, 85%.

Example 9

Synthesis of C6-OHP.Cl

A 0.47 g portion of l-OHP.Cl was dissolved in 40 ml of $H_2O$+MeOH mixture solution, and the solution was mixed with 0.19 g of 1M C6-COOAg and stirred for 48 hours at room temperature in the dark. Thereafter, the same treatment as in Example 4 was repeated. Yield, 0.45 g, 85%.

Example 10

Synthesis of C4-OHP.Cl

Reaction of l-OHP.Cl and C4-COOAg was carried out in the same manner as described in Examples 8 and 9. Yield, 0.45 g, 85%.

Analytical data of the thus obtained complexes are shown below.

1. Elemental analysis

|  | C | H | N | Pt |
|---|---|---|---|---|
| C4-OHP · Cl, $C_{12}H_{27}N_2O_6PtCl$ | | | | |
| calcd. | 27.74; | 4.04; | 5.39 | |
| found | 27.84; | 4.75; | 5.57 | |
| C5-OHP · Cl, $C_{13}H_{29}N_2O_6PtCl$ | | | | |
| calcd. | 29.26; | 4.31; | 5.25 | |
| found | 29.16; | 4.95; | 5.10 | |
| C6-OHP · Cl, $C_{14}H_{31}N_2O_6PtCl$ | | | | |
| calcd. | 30.68; | 4.56; | 5.11; | 35.61 |
| found | 29.69; | 4.78; | 5.03; | 35.00 |
| C5-OHP · Br, $C_{13}H_{29}N_2O_6PtBr$ | | | | |
| calcd. | 26.98; | 3.97; | 4.87 | |
| found | 26.94; | 4.02; | 4.87 | |
| C6-OHP · Br, $C_{14}H_{31}N_2O_6PtBr$ | | | | |
| calcd. | 28.37; | 4.22; | 4.72 | |
| found | 27.36; | 4.03; | 4.59 | |
| C5-OHP · I, $C_{13}H_{29}N_2O_6PtI$ | | | | |
| calcd. | 24.96; | 3.68; | 4.48 | |
| found | 24.85; | 3.57; | 4.40 | |
| C6-OHP · I, $C_{14}H_{31}N_2O_6PtI$ | | | | |
| calcd. | 26.29; | 3.19; | 4.38 | |
| found | 26.30; | 3.20; | 4.40 | |

2. Partition coefficient

Partition coefficient (PC) of each of the thus obtained complexes to 1-octanol/water is as follows.

| Complex | PC |
|---|---|
| C4—OHP · Cl | $3.6 \times 10^{-2}$ |
| C5—OHP · Cl | $2.4 \times 10^{-1}$ |
| C6—OHP · Cl | $8.4 \times 10^{-1}$ |
| C7—OHP · Cl | 2.7 |

3. Solubility

Solubility of each of the thus obtained complexes in water (about 20° C.) is shown below.

| Complex | Solubility (mM) |
|---|---|
| C4—OHP · Cl | 147 |
| C5—OHP · Cl | 41 |
| C6—OHP · Cl | 9.6 |
| C7—OHP · Cl | 2.2 |

4. Stability

Stability of each of the thus obtained complexes in an aqueous solution of hydrochloric acid at 37° C. is shown below in terms of its half life.

| | Half life (hour) | |
|---|---|---|
| Complex | 0.05 M HCl | 1 M HCl |
| C4—OHP · Cl | >50 | 6.1 |
| C5—OHP · Cl | >50 | 7.4 |
| C6—OHP · Cl | N.D. | 8.9 |
| C7—OHP · Cl | N.D. | 11.3 |

The term N.D. indicates that significant decrease in concentration was not observed. The measurement was carried out at a complex concentration of 50 $\mu$M at 37° C. in the dark.

5. Reduction property

Test results of the in vitro reduction of the thus obtained complexes by an ascorbic acid salt are shown below in terms of half life.

| | Half life (hour) | |
|---|---|---|
| Complex | 5 mM | 100 mM |
| C4—OHP · Cl | 0.6 | <0.1 |
| C5—OHP · Cl | 0.8 | <0.1 |
| C6—OHP · Cl | 1.2 | <0.1 |
| C7—OHP · Cl | 1.6 | <0.1 |

The measurement was carried out at a complex concentration of 50 $\mu$M, pH 7.5 (50 mM HEPES-NaOH buffer), at 37° C. in the dark.

Carcinostatic Test ip: On the day 0, L 1210 ($10^5$ cells/mouse) was transplanted into the abdominal cavity of each $CDF_1$ mouse, and each of the platinum complexes was intraperitoneally administered on the day 1, day 5 and day 9 (Q04D×03). Using 5 animals in one group, T/C % (T: treated, C: control) is calculated from survived days. A T/C % value of 125 or more was judged effective. The number of survived (or tumor bearing) animals is shown as n/5. A total of 10 mice were used in the control.

The results are shown below.

Carcinostatic effect ip—ip, L 1210, three administrations on days 1, 5 and 9

| | 100 | 50 | 25 | 12.5 | mg/kg dose |
|---|---|---|---|---|---|
| C4—OHP · Cl | T 63 | 195 | 145 | 130 | T/C% |
| C5—OHP · Cl | T 88 | 283 (4/5) | 168 | | |
| C6—OHP · Cl | T 80 | 280 (1/5) | 173 | | |
| C7—OHP · Cl | | 176 | 137 | 122 | |
| C5—OHP · Br | | 107 | 395 (4/5) | | |
| C6—OHP · Br | T 69 | T 96 | 373 (4/5) | | |

T = toxic

L 1210 ($10^5$ cells/mouse), one group=5 $CDF_1$ mice, ip administration on the days 1, 5 and 9.

po: On the day 0, L 1210 ($10^5$ cells/mouse) was transplanted into the abdominal cavity of each $CDF_1$ mouse, and each of the platinum complexes was orally administered on the day 1, day 3, day 5, day 7 and day 9 (Q02D×05), or on the day 1 to day 5 (Q01D×05). The oral administration was carried out with a 10, 7.5 or 5 times higher dose than the optimum amount of each platinum complex by ip (T/C % of ip; 100 mg/kg, 75 mg/kg or 50 mg/kg, respectively). A value of 140% or more was judged effective.

The results are shown below.

(Oral) carcinostatic effect L 1210, ip-po, every two days Q02D×05

| | mg/kg dose | | | |
|---|---|---|---|---|
| | 15 | 10 | 5 | 2.5 |
| C5—OHP · Cl | T 60 | 143 | 214 | 140 |
| C6—OHP · Cl | T 98 | 168 | 191 | 143 |
| C7—OHP · Cl | | 151 | 129 | 117 |
| C5—OHP · Br | T 73 | 163 | 160 | |
| C6—OHP · Br | T 88 | 180 | 173 | |

T = toxic

L 1210 ($10^5$ cells/mouse); one group=5 $CDF_1$ mice; Suspension in olive oil was administered into the stomach through a catheter.

I claim:

1. A platinum(IV) complex represented by the general formula (I):

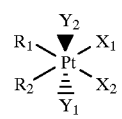

(I)

wherein $R_1$ and $R_2$ independently represent ammonia, an alkylamine or a cycloalkylamine, or $R_1$ and $R_2$ may together form a 1,2-cycloalkyldiamine; $X_1$ and $X_2$ independently represent a halogen, nitrate ion, sulfate ion or a monocarboxylic acid, or $X_1$ and $X_2$ may together form a glycolate or a dicarboxylic acid; $Y_1$ represents formic acid, a $C_1$–$C_8$ alkyl-monocarboxylic acid, alkenyl-monocarboxylic acid, aryl-monocarboxylic acid, aralkyl-monocarboxylic acid, alkylamino-monocarboxylic acid or alkoxyl-monocarboxylic acid or sulfonic acid; and $Y_2$ represents a halogen.

2. The complex according to claim 1 wherein it is represented by the general formula (II):

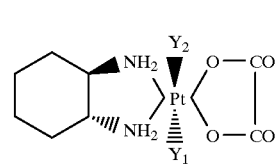

(II)

wherein $Y_1$ and $Y_2$ are as defined in the general formula (I).

3. The complex according to claim 2 wherein $Y_1$ is a $C_2$–$C_8$ alkyl monocarboxylic acid and $Y_2$ is a halogen.

4. A carcinostatic agent which comprises an effective amount of the platinum(IV) complex of claim 1 as an active ingredient.

5. A process for producing a platinum(IV) complex

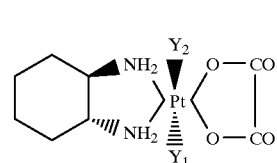

(II)

wherein $Y_1$ is a $C_2$–$C_8$ alkyl monocarboxylic acid and $Y_2$ is a halogen which comprises allowing a compound represented by the general formula (III):

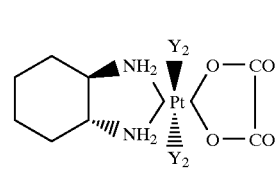

(III)

(wherein $Y_2$ represents a halogen) to react with a silver salt of a $C_2$–$C_8$ alkyl monocarboxylic acid.

6. A process for producing a platinum(IV) complex

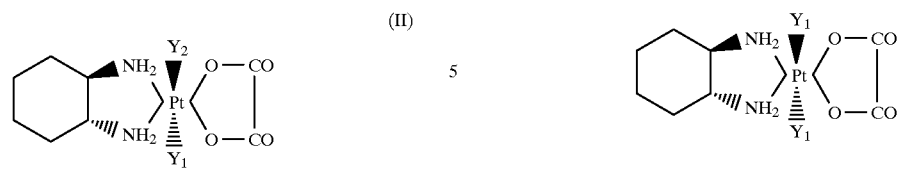

$Y_1$ represents formic acid, a $C_1$–$C_8$ alkyl-monocarboxylic acid, alkenyl-monocarboxylic acid, aryl-monocarboxylic acid, aralkyl-monocarboxylic acid, alkylamino-monocarboxylic acid or alkoxyl-monocarboxylic acid or sulfonic acid; and $Y_2$ represents a halogen which comprises allowing a compound represented by the general formula (IV):

(wherein $Y_1$ is as defined for general formula to react with a hydrogen halide.

7. A carcinostatic agent comprising an effective amount of the platinum (IV) complex of claim 2.

8. A carcinostatic agent comprising an effective amount of the platinum (IV) complex of claim 3.

* * * * *